United States Patent
Preslicka

(10) Patent No.: US 11,534,332 B1
(45) Date of Patent: Dec. 27, 2022

(54) BLOOD FLOW DIRECTION FAVORING CONDOM

(71) Applicant: David Preslicka, Sidney, NE (US)

(72) Inventor: David Preslicka, Sidney, NE (US)

( * ) Notice: Subject to any disclaimer, the term of this patent is extended or adjusted under 35 U.S.C. 154(b) by 0 days.

(21) Appl. No.: 15/786,331

(22) Filed: Oct. 17, 2017

(51) Int. Cl.
*A61F 6/00* (2006.01)
*A61F 6/04* (2006.01)

(52) U.S. Cl.
CPC .......... *A61F 6/04* (2013.01); *A61F 2006/047* (2013.01); *A61F 2006/048* (2013.01)

(58) Field of Classification Search
CPC . A61F 6/04; A61F 2006/047; A61F 2006/048
USPC ........................................................ D24/105
See application file for complete search history.

(56) References Cited

U.S. PATENT DOCUMENTS

| | | | |
|---|---|---|---|
| 4,320,752 A * | 3/1982 | Comparetto | A61F 6/04 128/844 |
| 4,373,776 A | 2/1983 | Purdy | |
| 4,798,600 A * | 1/1989 | Meadows | A61F 6/04 128/839 |
| 4,852,586 A * | 8/1989 | Haines | A61F 6/04 128/842 |
| 4,881,553 A * | 11/1989 | Grossman | A61F 6/04 128/844 |
| 5,313,546 A | 5/1994 | Toffetti | |
| 5,727,097 A | 3/1998 | Lee et al. | |
| 5,732,174 A | 3/1998 | Carpenter et al. | |
| 6,431,763 B1 | 8/2002 | Sherman et al. | |
| 6,450,697 B1 | 9/2002 | Ngo | |
| 6,569,083 B1 * | 5/2003 | Kassman | A61F 5/41 128/842 |
| 6,579,014 B2 | 6/2003 | Melton et al. | |
| 6,607,308 B2 | 8/2003 | Dair et al. | |
| 7,359,613 B2 | 4/2008 | Mullaney et al. | |
| 7,597,485 B2 | 10/2009 | Moriarty et al. | |
| 7,927,023 B2 | 4/2011 | Moriarty et al. | |
| 2011/0206328 A1 | 8/2011 | Wang | |
| 2012/0073580 A1 * | 3/2012 | Chuah | A61F 6/04 128/844 |
| 2013/0014764 A1 * | 1/2013 | Rojas | A61F 6/04 128/844 |
| 2018/0000632 A1 * | 1/2018 | Yun | A61F 6/04 |

* cited by examiner

*Primary Examiner* — Steven O Douglas
(74) *Attorney, Agent, or Firm* — Leyendecker & Lemire

(57) ABSTRACT

A condom that extends along a central axis and has a series of ribs along an internal surface of the condom. The ribs having a concave surface that encounters blood flow from the heart, and thus uses the blood flow to urge the rib away from the central axis. The ribs also include a wall that is positioned so as to encounter the blood flow returning to the heart, the wall being vertical or concave, so as to not urge the rib away from the central axis of the condom.

1 Claim, 2 Drawing Sheets

BLOOD FLOW DIRECTION FAVORING CONDOM

BACKGROUND OF THE INVENTION

(a) Field of the Invention

This application relates to condoms for males, the condoms having internal projections for promoting blood flow in a preferential direction for maintaining an erection.

(b) Discussion of Known Art

The blood-flow mechanism by which an erection is achieved is reasonably well understood. The nervous system allows the fibers of the dorsal artery to relax in response a response to certain stimulation. The relaxation of the dorsal artery allows increased blood flow into the penis. This increased blood flow allows the fibers of the corpora cavernosa to fill with blood. Additionally, blood flow out of the penis through the deep artery is inhibited by the flow and retention of the blood by the expansion of the corpora. Thus, the increased blood flow expands the sinusoidal spaces in the corpora and the penis becomes erect. More specifically, blood from the body enters the penis through the profunda and dorsal arteries. Blood is then circulated through the penis and accumulated in corpora, and then leaves the organ through the subcutaneous dorsal vein, and then the deep dorsal veins and the subcutaneous lateral veins of the penis. See U.S. Pat. No. 3,636,948 to Atchley, incorporated herein by reference, at Cols. 42-50.

Atchley discloses a band or "strip" that includes various protrusions along the strip. The protrusions are positioned to provide pressure on locations of the penis so as to restrict blood flow at locations where blood flows from the penis, and thus the device promotes retention of blood in the penis. Others have attempted to provide mechanical erection assistance devices that aid the retention of blood within the corpora. For example, U.S. Pat. No. 3,455,301 to Clark, presents a blood-flow constriction device.

Important disadvantages with these devices are that they act along a very focused section along the penis, and thus are anticipated to require inordinate amounts of localized pressure to be effective. Additionally, devices such as the Atchley device must also be positioned at the correct radial position about the penis in order to impose pressure at the locations indicated by Atchley. This positioning is likely to be difficult and unreliable due to differences in individual anatomy.

Accordingly, a review of known devices reveals that a need remains for a device for aiding in the control of blood to and from the penis while erect.

SUMMARY

It has been discovered that the problems left unanswered by known art can be solved by providing a condom that favors blood flow to into the penis, while presenting at least some differential impedance of flow away from the penis includes:

A condom having a body comprising an elongated concave sheath that extends along a central axis, the sheath having an outer surface, a first end having an opening adapted for accepting the penis, and a second end that is closed, the sheath further having an inner surface along the inside of the concave sheath from the first end to the second end of the sheath; and At least one, but preferably several radial ribs that protrude from the inner surface towards the central axis of the sheath, at least one, but preferable each rib having a forward surface that extends away from the inner surface of the sheath and towards the axis of the sheath, so that the forward surface is generally concave and generally conical;

The forward surface terminating at a generally cylindrical surface, the generally cylindrical surface extending from the forward surface towards the second end of the condom, and terminating at a generally planar wall that extends from the inner surface to the generally cylindrical surface, preferably in a normal direction form the central axis, so that when the condom is worn on the penis, the forward surface of each of the radial ribs present a gradual increase in impedance to the flow of blood through the profunda and dorsal arteries as the blood flows towards the second end of the sheath, and so that the generally cylindrical surface restricts the flow of blood along the cylindrical surface, providing greater impedance to blood flow from the from the second end of the sheath towards the first end of the sheath, and so that blood pressure in the profunda and dorsal arteries is favored to progressively increase along the penis from a location at the first end of the sheath towards the second end of the sheath.

It should also be understood that while the above and other advantages and results of the present invention will become apparent to those skilled in the art from the following detailed description and accompanying drawings, showing the contemplated novel construction, combinations and elements as herein described, and more particularly defined by the appended claims, it should be clearly understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which.

DETAILED DESCRIPTION OF PREFERRED EXEMPLAR EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
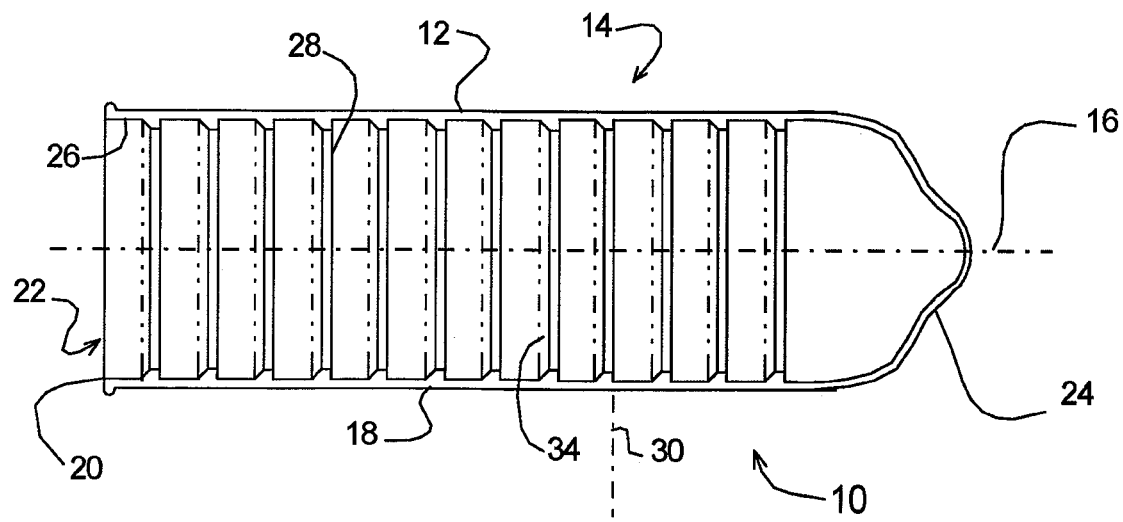
FIG. 1 is cross-section along the length of an embodiment of the invention, the view illustrating an example of the forward, cylindrical and aft surfaces of the ribs.
Figure 2:
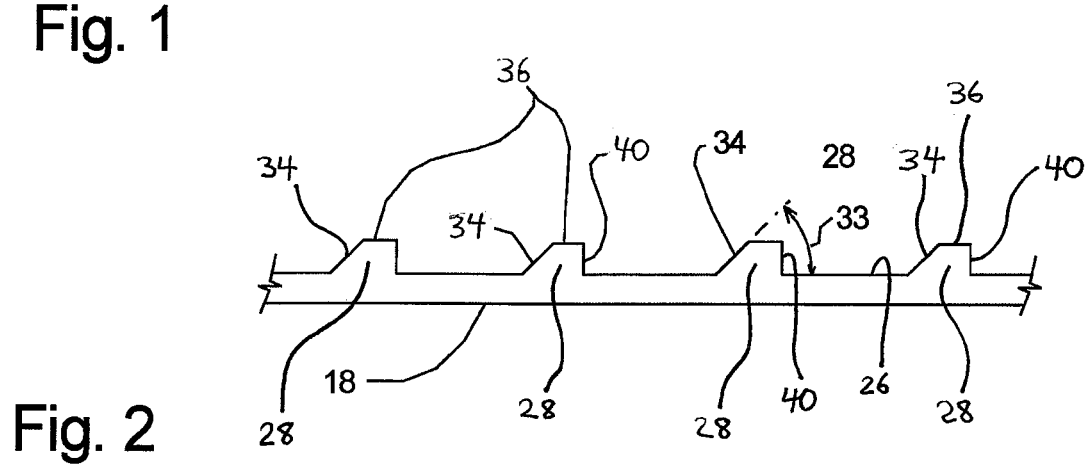
FIG. 2 illustrates a cross-section of an example of the ribs.
Figure 4:
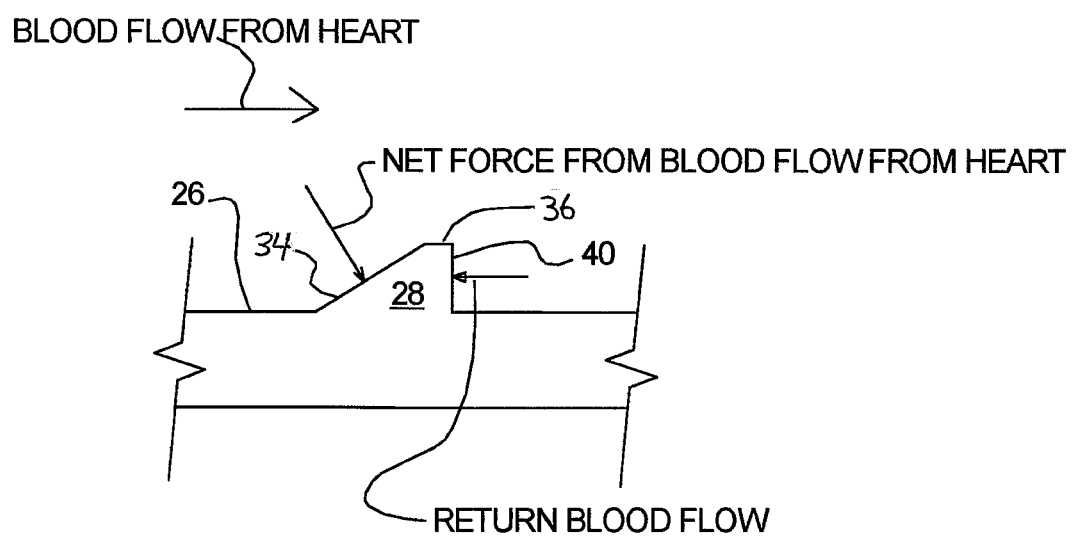
FIG. 4 illustrates the fluid flow forces against the ribs as shown in the example illustrated in FIG. 2.

Turning now to FIGS. 1, 2, and 4 it will be understood that that a condom 10 having a body 12 shaped as an elongated concave sheath 14 has been disclosed. The elongated sheath extends along an axis 16, the sheath having an outer surface 18, a first end 20 having an opening 22 for accepting the penis, and a second end 24 that is closed. The example shown in FIG. 1 shows the sheath 14 as having an inner surface 26. The illustrated example shows that the inner surface 26 of the concave sheath 14 extends from the first end 20 to the second end 24 of the sheath. The illustrated sheath 14 is also shown including several radial ribs 28 that protrude from the inner surface 26 towards the axis 16 of the sheath 14. Each rib 28 extends about a plane that is at a right angle to the axis 16, such as the dashed line 30 representing a plane associated with one rib.

As illustrated in FIGS. 2 and 4, each rib will preferably include a forward surface 34 that extends away from the inner surface 26 of the sheath 14, and will be at an angle 33 to the axis 16. Thus, the forward surface 34 will extend towards the second end 24, so that each rib 28 a closed, continuous surface extending no more than 360 degrees about the axis 16. Accordingly, the illustrated examples of the ribs 28 each create a concave, generally conical, internal forward surface 34 along the sheath when the sheath is expanded in a radial direction about the axis 16.

Additionally, it is contemplated that in an example the forward surface 34 terminates at a cylindrical ridge surface 36 that creates a flat ring when the generally cylindrical sheath 14 is expanded in a radial direction about the axis 16. Still further, the flat ring will extend from the forward surface 34 and terminate at a generally planar wall 40 that extends from the inner surface 26 to the cylindrical ridge surface 36 of the flat ring, so that when the condom is worn on the penis, the forward surface of each of the ribs provides a gradually increasing impedance to the flow of blood through the profunda and dorsal arteries as the blood flows from the first end 20 of the sheath towards the second end 24 of the sheath 14.

It will be understood that the provision of several generally cylindrical ridge surfaces 36 will provide a consistently increasing retention of blood as the blood flows from the first end 20 of the sheath 14 towards the second end 24 of the sheath 14. This will provide increasing blood pressure in the profunda and dorsal arteries in a progressive manner along the penis, from a location at the first end 20 of the sheath towards the second end 24 of the sheath.

Still further, it will be understood that the use of a conical surface on the side that faces the first end 20 of the sheath will allow the device to provide a radial force against the concave surface 34, lifting the cylindrical ridge surface 36 of the flat ring away from the central axis 16. This will facilitate blood flow past the flat ring. However, return blood flow, from the second end 24 towards the first end 20 of the sheath 14 (i.e., returning towards the heart) will encounter the flat planar wall 40, which will simply impede flow back towards the heart. Thus the interaction of the returning blood flow will not result in a net lifting force on the radial rib 28, and will not urge the radial rib or the cylindrical ridge surface 36 of the flat ring to move away from the central axis 16. Accordingly, pressure blood flowing back, away from the second end 22 of the sheath will not produce a net lifting force on the flat ring 32, which will favor retention of blood between the flat wall and the second end 22, making more blood available for accumulation in the corpora and promoting the erection of the penis.

Figure 3:
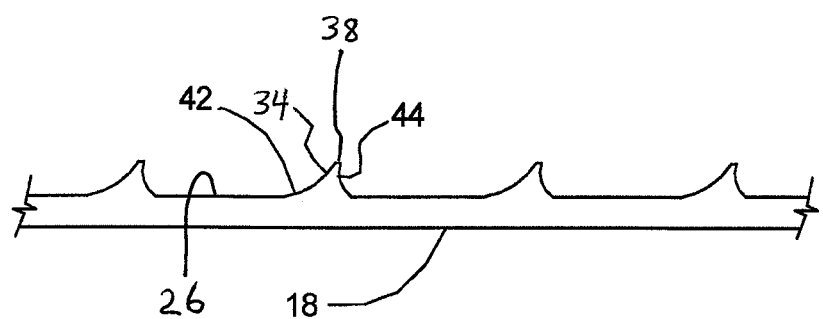
FIG. 3 illustrates a cross-section of another example of the ribs.

Referring to FIG. 3 it will be understood that it is contemplated that the transition between the concave surface 34 and the inner surface 26 may incorporate a radius 42. Additionally, the distal terminus of each ridge or flat ring 38 may be positioned over a concave aft wall 44 instead of a planar wall 40. Additionally, the flat ring 38 may include radiused transitions between the concave surface 34 and the concave aft wall.

It can be appreciated that the above-described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. A condom comprising a body comprising an elongated sheath that extends along an axis, the sheath having an outer surface; a first end having an opening adapted for accepting a penis, and a second end that is closed, the sheath further having an inner surface along the inside of the sheath from the first end to the second end of the sheath; and several radial ribs that protrude from the inner surface towards the axis of the sheath, each rib having a forward surface that extends away from the inner surface of the sheath and towards the axis of the sheath, so that the forward surface is generally concave and generally conical;

the forward surface terminating at a generally cylindrical surface, the generally cylindrical surface extending from the forward surface and terminating at a generally planar wall that extends from the inner surface, so that when the condom is worn on the penis, the forward surface of each of the ribs provides a gradual increase in impedance to the flow of blood towards the second end of the sheath, and so that the generally cylindrical surface restricts the flow of blood from the second end of the sheath towards the first end of the sheath, and so that blood pressure in the profunda and dorsal arteries is favored to progressively increase along the penis from a location near the first end of the sheath towards the second end of the sheath.

\* \* \* \* \*